(12) United States Patent
Magno et al.

(10) Patent No.: US 12,239,339 B2
(45) Date of Patent: Mar. 4, 2025

(54) COLLAPSIBLE HANDLE DESIGN FOR DEBRIDERS

(71) Applicant: GYRUS ACMI, INC., Westborough, MA (US)

(72) Inventors: Joey Magno, Dudley, MA (US); I. Miroslava Avila, Bristol, CT (US)

(73) Assignee: Gyrus ACMI, Inc., Westborough, MA (US)

( * ) Notice: Subject to any disclaimer, the term of this patent is extended or adjusted under 35 U.S.C. 154(b) by 186 days.

(21) Appl. No.: 17/650,181

(22) Filed: Feb. 7, 2022

(65) Prior Publication Data

US 2022/0249116 A1  Aug. 11, 2022

Related U.S. Application Data

(60) Provisional application No. 63/147,728, filed on Feb. 9, 2021.

(51) Int. Cl.
*A61B 17/32* (2006.01)
*A61B 17/3205* (2006.01)
*A61B 17/00* (2006.01)

(52) U.S. Cl.
CPC ...... *A61B 17/3205* (2013.01); *A61B 2017/00424* (2013.01); *A61B 2017/00469* (2013.01); *A61B 2017/320004* (2013.01); *A61B 2217/005* (2013.01)

(58) Field of Classification Search
CPC .............. A61B 17/2909; A61B 17/295; A61B 17/32; A61B 17/32002; A61B 17/3205; A61B 2017/00424; A61B 2017/00446; A61B 2017/0046; A61B 2017/291; A61B 2017/2925; A61B 2017/320024; A61B 2017/320028; A61B 2017/320032; A61B 2017/32007; A61F 2/9517

See application file for complete search history.

(56) References Cited

U.S. PATENT DOCUMENTS

| | | | | |
|---|---|---|---|---|
| 5,782,749 | A | * | 7/1998 | Riza ................... A61B 17/2909 600/117 |
| 2009/0171147 | A1 | * | 7/2009 | Lee ........................ A61B 17/29 600/137 |
| 2011/0190801 | A1 | * | 8/2011 | Mark ..................... A61B 17/32 606/170 |
| 2011/0301577 | A1 | * | 12/2011 | Simmen ................. A61B 17/16 606/1 |
| 2018/0042591 | A1 | * | 2/2018 | Russo .................. A61B 17/064 |

* cited by examiner

*Primary Examiner* — Diane D Yabut
*Assistant Examiner* — Christian D Knauss
(74) *Attorney, Agent, or Firm* — Schwegman Lundberg & Woessner, P.A.

(57) ABSTRACT

A medical device for debridement can include an elongate housing, a shaft extending through the housing and distally therefrom, a drive to manipulate the cutter, and a collapsible handle than can to couple with the housing. An elongate grip of the handle can turn aft and be at least partially disposed in the elongate housing for use of the device with pen grip. The elongate grip of the handle can turn fore and extend distally from the housing for use of the device with pistol grip.

5 Claims, 9 Drawing Sheets

COLLAPSIBLE HANDLE DESIGN FOR DEBRIDERS

CROSS-REFERENCE TO RELATED APPLICATIONS

This application claims the benefit of priority to U.S. Provisional Patent Application Ser. No. 63/147,728, filed Feb. 9, 2021, the content of which is incorporated herein by reference in its entirety.

TECHNICAL FIELD

This document pertains generally, but not by way of limitation, to devices and methods for debridement.

BACKGROUND

In a medical procedure, such as debridement, a medical device can be used to remove portions of tissue, bone, and/or other objects from a surgical site. The medical device can be a shaver, a debrider, a microdebrider, morcellator, or other suitable device for debridement. The medical device can have a cutting portion extending from a housing. During the procedure, the housing can be held by a professional and positioned relative to a patient such as to provide precise and careful removal of objects. Modern debriders can incorporate various minimally intrusive cutting mechanisms to shorten recovery time from the procedure. In such minimally intrusive cutting mechanisms, the cutter can be partially enclosed such as to only allow for cutting in a small window of the cutting mechanism. A shaft supplying the cutter can also be curved such as to enable further precision. Axial rotation of the elongated housing of the medical device can alter the direction of a cutting window and/or the angle of the cutting portion.

SUMMARY

In an approach to debridement, a medical device can be used such as to abrade and remove portions of tissue or other objects. A medical device can have a cutting mechanism which can be rotatable relative to a housing by manipulation of a nosecone. One example of a medical device can have a housing without a handle and can be gripped by the professional like a pen between a thumb, index finger, and middle finger. Some professionals can prefer pen grip for certain placements and procedures of debridement. Devices designed for pen grip can include a stub extending from the housing. The stub can be gripped by the middle finger during pen grip for further security. Another example of a medical device can have a housing connected to a handle and can be gripped by the professional like a pistol. Some professionals can prefer the pistol grip for certain placements and procedures of debridement and can utilize the ergonomic ease of manipulating the nosecone while the housing is securely anchored by hold of the handle.

Optimal grip of the device can vary among professionals across procedures depending on user hand size and shape, user technique, surgical site location, and other factors. The present inventors have recognized, among other things, that the limited available grip orientations available to a user of a medical device can create the need to alternate between multiple devices or can cause the professional to undertake the procedure without optimal ergonomic position of the device.

Aspect 1 can include or use a medical device for tissue removal, and the medical device can include or use an elongate housing, a shaft extending through the elongate housing and distally therefrom, the shaft containing a cutter configured such as to sever tissue, a drive configured such as to rotate the cutter, reciprocate the cutter, or both, and a handle configured such as to couple with the housing, the handle including or using a truncate stub and an elongate grip pivotably coupled to the truncate stub. In Aspect 2, the medical device of Aspect 1 can optionally be configured such that the shaft can be coupled with a vacuum portion configured to supply remote suction to a lumen of the shaft. In Aspect 3, the medical device of Aspect 1 and/or Aspect 2 can be optionally configured such that the elongate grip can be configured such as to pivotably alternate between a collapsed position wherein the elongate grip can be closed aft and at least partially disposed in a cavity in the elongate housing and a deployed position wherein the elongate grip can open fore and can extend distally from the elongate housing. In Aspect 4, the medical device of any one or any combination of Aspects 1-3 can optionally be configured such that the elongate grip can be pivotably coupled to the truncate stub at a first end of the elongate grip, the first end of the elongate grip including or using an eccentric locking cam configured such as to engage on the elongate housing when the grip is in the deployed position. In Aspect 5, the medical device of any one or any combination of Aspects 1-4 can optionally be configured such that the truncate stub can be slidably coupled to the elongate housing. In Aspect 6, the medical device of any one or any combination of Aspects 1-5 can optionally be configured such that the truncate stub can be slidably coupled to the elongate housing at least one longitudinal groove of the elongate housing. In Aspect 7, the medical device of any one or any combination of Aspects 1-6 can optionally be configured such that cam pressure on the elongate housing can restrict travel of the truncate stub relative to the elongate housing. In Aspect 8, the medical device of any one or any combination of Aspects 1-7 can optionally be configured to include or use a grip lock configured such as to retain the elongate grip in the collapsed position. In Aspect 9, the medical device of any one or any combination of Aspects 1-8 can optionally be configured such that the grip lock can restrict travel of the truncate stub within the longitudinal groove when the elongate grip is held in the collapsed position. In Aspect 10, the medical device of any one or any combination of Aspects 1-9 can optionally include or use a grip cover configured to slide over the elongate grip. In Aspect 11, the medical device of any one or any combination of Aspects 1-10 can optionally include or use a collapsible handle for use with a medical instrument, and the handle can include or use a truncate stub configured such as to couple to a medical instrument and an elongate grip pivotably connected to the truncate stub, the elongate grip being configured such as to pivotably alternate between a collapsed position wherein the elongate grip can be closed aft and at least partially disposed in a cavity in an elongate housing of the medical instrument and a deployed position wherein the elongate grip can open fore and extends distally from the elongate housing. In Aspect 12, the medical device and/or handle of any one or any combination of Aspects 1-11 can optionally be configured such that the truncate stub can be slidably coupled to the elongate housing. In Aspect 13, the medical device and/or handle of any one or any combination of Aspects 1-12 can optionally be configured such that the truncate stub can be slidably coupled to the elongate housing in at least one longitudinal groove of the elongate housing. In Aspect 14, the medical device and/or handle of any one or any combination of Aspects 1-13 can optionally be configured such that the elongate grip can be pivotably coupled to the truncate stub at a first end of the elongate grip, the first end of the elongate grip including or using an eccentric locking cam configured to engage on the elongate housing when the elongate grip is in the deployed position. In Aspect 15, the medical device and/or handle of any one or any combination of Aspects 1-14 can optionally be configured such that cam pressure on the elongate housing can restrict travel of the truncate stub relative to the elongate housing. In Aspect 16, the medical device and/or handle of any one or any combination of Aspects 1-15 can optionally be configured such that a grip lock on the elongate housing can restrict travel of the truncate stub within the longitudinal groove when the elongate grip is held in the collapsed position. In Aspect 17, the medical device and/or handle of any one or any combination of Aspects 1-16 can optionally be configured to include or use a method of using a medical device with a collapsible handle, and the method can include or use turning an elongate grip about a pivot on a truncate stub, positioning a cutter at a distal end of a shaft, the shaft extending through the elongate housing and distally therefrom, and severing tissue with the cutter. In Aspect 18, the medical device, handle and/or method of any one or any combination of Aspects 1-17 can optionally be configured such that turning can further include or use closing the elongate grip aft about the pivot and at least partially disposing the grip in a cavity in the elongate housing. In Aspect 19, the medical device, handle and/or method of any one or any combination of Aspects 1-18 can optionally be configured such that turning further can include or use opening the elongate grip fore and extending the grip distally from the housing. In Aspect 20, the medical device, handle and/or method of any one or any combination of Aspects 1-19 can optionally include or use sliding the truncate stub along at least one longitudinal groove in the elongate housing. Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1:
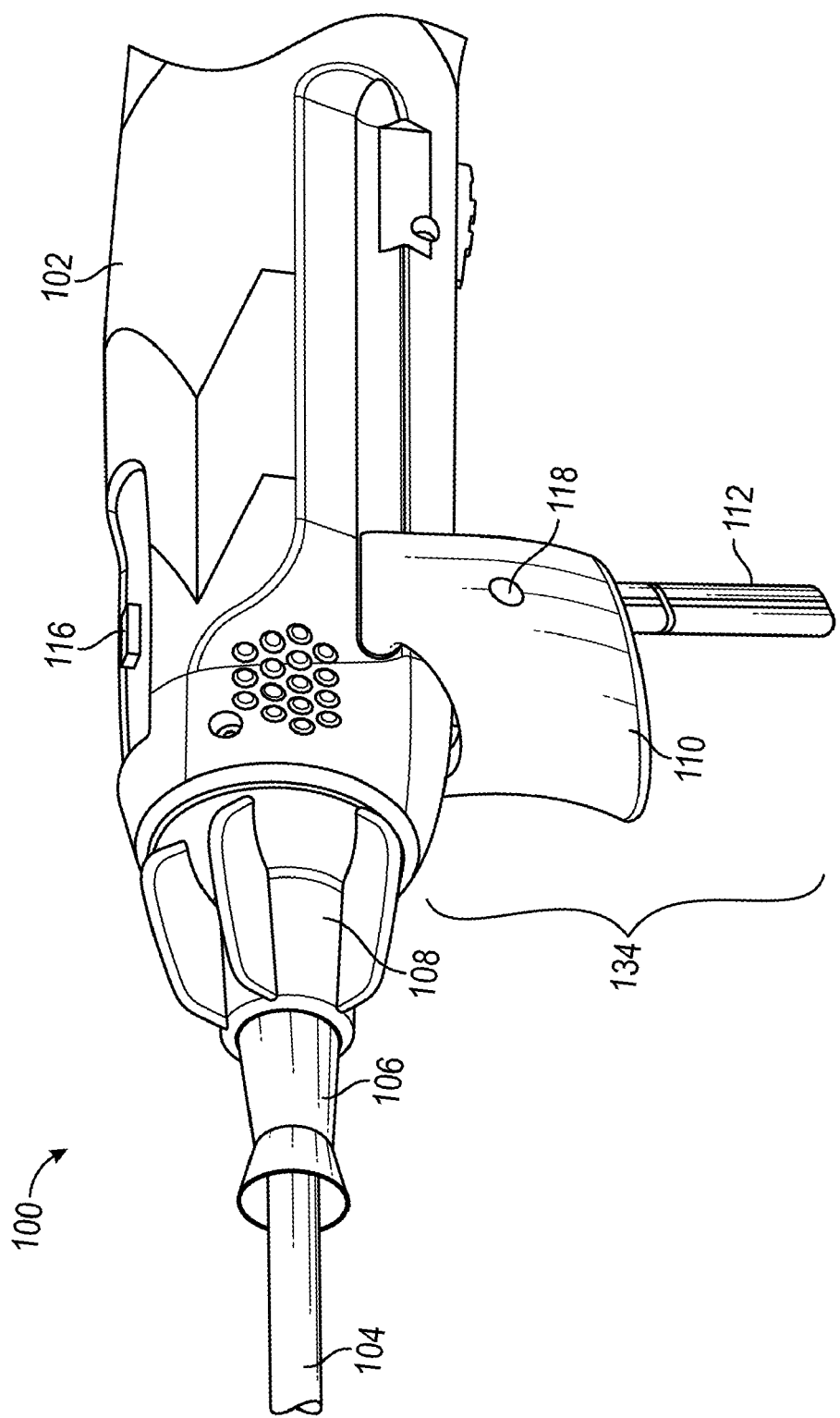
FIG. 1 is a perspective view of a debrider.

The present disclosure, in one or more embodiments, relates to devices and methods for surgical debridement. More particularly, the present disclosure relates to an adjustable debrider and methods for versatile and precise debridement. A debridement procedure can be undergone to remove dead, damaged, necrotic, or infected tissue or other objects from a surgical site. A medical device such as a debrider, multidebrider, microdebrider, shaver, or other device can be utilized for selective, minimally invasive debridement. Debridement can be used to remove bone or tissue in ear, laryngeal, paranasal, nasal, uterine, tonsil, adenoid, and skull base surgeries. Debridement can also be used for other beneficial surgical purposes and at other surgical sites.

A debrider can include or use a handpiece, referred to herein as an elongate housing, which can be coupled to a shaft, also referred to herein as a blade. The debrider can be connected to other elements in a debridement system, such as a power supply, suction supply, irrigation line, motor control unit, declog valves, or other elements. The debrider can function to cut, shave, or drill material from a surgical site and can facilitate aspiration of the material from the site and to a collection cannister or other destination. The blade can be removably coupled to the housing and can be sized and shaped according to the specific surgical site. Accordingly, a professional can interchangeably couple one of a wide variety of blades to the housing depending on the procedure at hand. Depending on the size and shape of the blade and the surgical site, a professional can alter technique and grip in using the debrider. The housing can also be sized and shaped according to a preferential technique of a professional or to accommodate operation at a specific site. Additional components can be paired to the housing to further modify the device for various uses. One approach to debridement is to use a completely disposable device manufactured for specific use at a particular site. This approach can be costly and prohibitive to a professional. Another approach to debridement is to use a reusable debrider housing outfitted with disposable components (i.e., a blade, a handle, or other components) sized and shaped for each specific procedure or technique. A problem with that approach, however, is that a professional must locate, assemble, and clean several parts to construct a device fit for the procedure. Further, the professional is limited during surgery to using the device-as-assembled and can be inhibited from dynamically altering their technique to meet the needs of the procedure at hand. The present devices and techniques can help avoid such problems because the device is easily and quickly adjustable to several configurations.

The present disclosure relates to, among other things, a device and method enabling debridement at multiple surgical sites. The device also can help reduce the number of exchanges of medical devices during a procedure and can increase ease and precision of debridement by a professional. The device can be configured to be held by a professional during debridement using any of several common techniques. Additionally, the device can be configured to be held by a collapsible handle or elongate grip of the handle. Alternatively or additionally, the device can be configured to be held by the device housing, and the elongate grip of the handle can recede to a collapsed position. The device, where the elongate grip is in the collapsed position, can be configured to be securely held and easily rotated due to presence of a truncate stub. The device can be configured to allow for various secure holding positions of the device with a dominant hand and ergonomic rotation of a nosecone with a non-dominant hand. Further, the device can be configured to allow for multiple points of connection of the handle along the length of the housing.

FIG. 1 shows a perspective view of an example of a debrider. A debrider 100 can include or use an elongate housing 102, a blade 106, a cutter 104, a nosecone 108, and an actuator 116. The housing 102 can be elongate and can be substantially cylindrically shaped. The housing 102 can also be substantially elliptically, cylindrically shaped. Diameters of housings 102 shaped as such can be within a range of about 0.25 inches to about 2 inches. In some examples, the housing diameters can be within the range of about 0.875 inches to about 1.25 inches. The housing 102 can be reusable, such as can be washable or autoclavable. Alternatively, the housing 102 can be disposable, its inner contents configurable to a new housing. The debrider 100 can also include or use a handle 134 coupled to the housing 102. The handle 134 can be not intended for removal from the housing 102 once it has been coupled. The handle can be unable to be removed from the housing 102 without excessive force or breakage once it has been coupled. The handle 134 can include or use a truncate stub 110 and an elongate grip 112 coupled to the truncate stub about a pivot point 118. The handle can additionally include or use a removeable grip cover 133 (see FIG. 2B). The blade 106 can be attached or coupled to the housing 102 and extend therefrom. The blade 106 can extend at least partially through the housing 102. The blade 106 can include or use a cutting mechanism, referred to herein as cutter 104. The blade 106 can be curved at a variety of different angles such as to allow for precision in placement of the cutter 104 during debridement. The cutter 104 can be a reciprocating or oscillating pair of cutting members, a rotating cutting member, or both. Alternatively or additionally, the cutter 104 can be a rotating burr. The cutter 104 can also be an electrode cutter. An illustrative example of an electrode cutter is described in U.S. patent application Ser. No. 15/936,678, filed on Mar. 27, 2018, and entitled Electrode Blade for Shavers, which is incorporated by reference herein in its entirety, including for its teaching of a medical device having an electrode blade, which can be used in combination with the debridement device described in the present disclosure. The cutter 104 can also include or use other mechanisms suitable for debridement blades. The cutter 104 can include a cutter window such as to focus the cutting action in a particular lateral direction relative to the blade 106. The housing can include or use a blade drive mechanism configured to drive the cutter 104. The blade drive mechanism can be an electric motor, a solenoid assembly, or other appropriate mechanism to move the cutter 104. For example, the cutter 104 can be motorized. The blade drive mechanism can be activated by an actuator 116. The actuator 116 can be a switch, a knob, a button, or other mechanism for actuation of the cutter 104. The actuator 116 can be located on the housing 102, such as located on the top of the housing as depicted in FIG. 1. The actuator 116 can be located at other locations on the housing, or alternatively or additionally can be located at a remote location, such as on a footswitch. The blade 106 can include or use a nosecone 108 at or near a blade connection point at a distal end of the housing 102. Turning the nosecone 108 about a medial axis of the housing 102 can cause rotation of the blade 106. Where the cutter 104 of the blade 106 has a cutter window, turning of the nosecone 108 can alter the lateral direction of the cutter window. Further, where the blade 106 is curved at an angle, turning of the nosecone 108 can alter the lateral direction in which the angled blade 106 extends. The debrider 100 can be itself a component of a larger debridement system. For example, the debrider 100 can be tethered to a source of suction, irrigation, or both via one or more connection lines 142 (see FIGS. 2A and 2B). Accordingly, the debrider 100 can provide aspiration and removal of tissue and other objects as they are shaved, cut, or drilled. For example, the debrider 100 can contain a port configured to supply remote suction and/or irrigation to a lumen of the blade or shaft 106. Aspiration can be a helpful feature of a debrider 100 with respect to cutting performance.

Figure 2A:
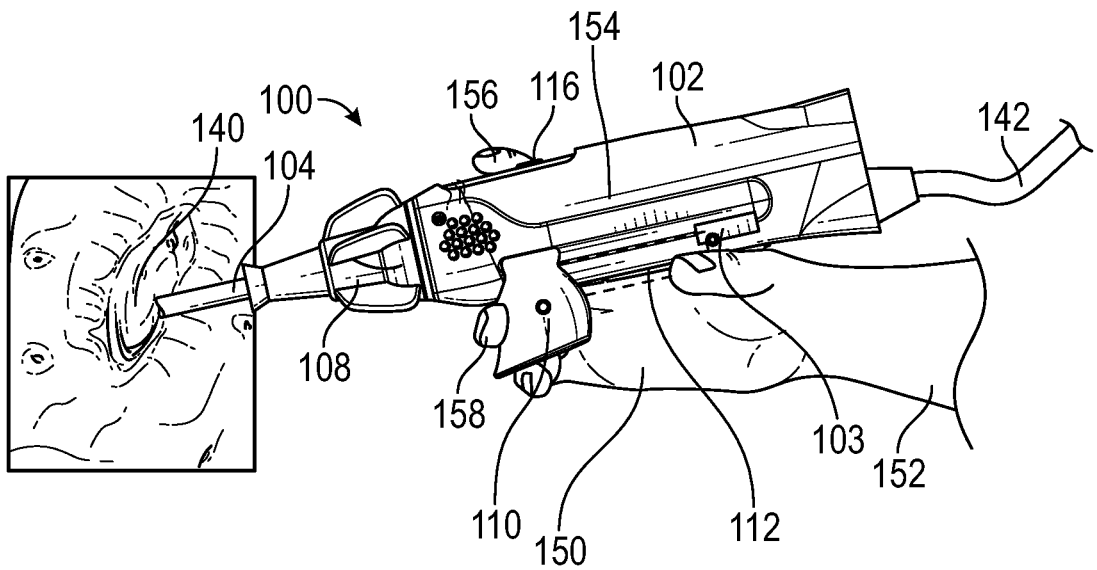
FIG. 2A is a side view of a debrider in operation with a pen grip.

FIG. 2A shows a side view of an example of a debrider in operation with a pen grip. A professional can hold or grasp the debrider 100 by the housing for certain procedures and techniques. Generally, such a hold can be referred to as "pen grip". FIG. 2A shows one way a professional can use the debrider 100 in pen grip. The housing 102 can rest at or near a dominant hand 150 between a thumb 154 and an index finger 156. While distinguished herein as the dominant hand 150 and the non-dominant hand, it is understood that either hand can be interchangeably used. The housing 102 can also rest at or near the middle finger 158, as shown. The professional can securely grip the housing between the thumb 154 and index finger 156 and further anchor the hold by gripping the truncate stub 110 with the middle finger 158. Other fingers, such as a ring finger or pinky finger can also be used to grip the truncate stub 110. Pen grip can enable a professional to have enhanced control and placement of the cutter 104 relative to the surgical site 140. For instance, pen grip with the truncate stub 110 as an anchor can enable secure, ergonomic rotation of the debrider 100 without excess strain on a wrist 152. Pen grip can further be advantageous for certain techniques and procedures depending on the professional's facility, hand size, and other factors. It can also be used to accommodate various individual patient anatomies and pathologies. In the collapsed position, the elongate grip 112 can be at least partially disposed in a cavity 103 of the housing 102. The elongate grip 112 can also be fully disposed in the cavity 103 of the housing 102 or can be collapsed parallel to the housing but not within a housing cavity. The debrider 100 can be used in pen grip without the elongate grip 112 extending distally from the housing 102 such as to avoid interference of the elongate grip 112 during the procedure.

Figure 2B:
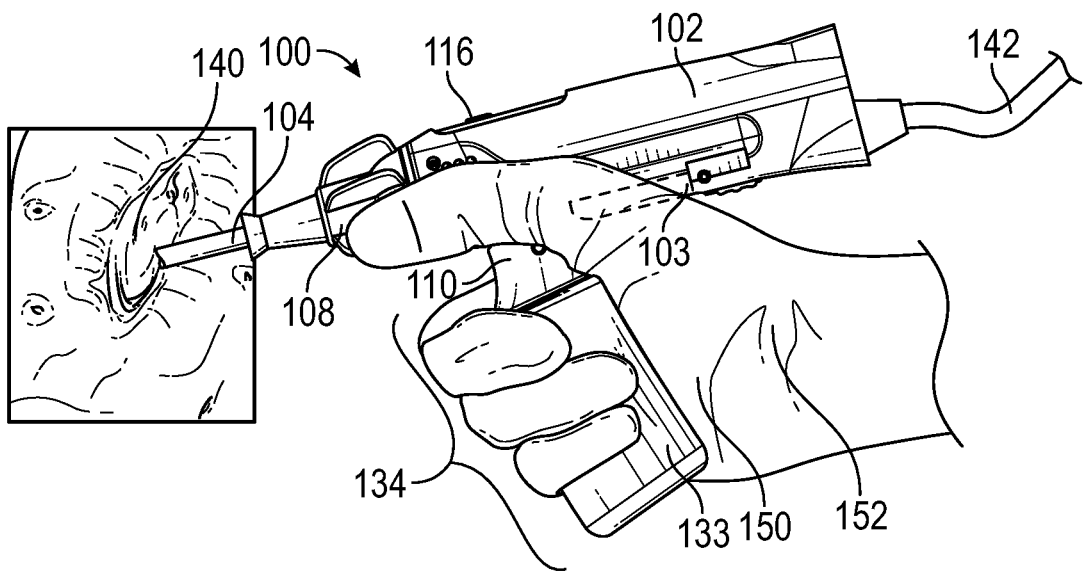
FIG. 2B is a side view of a debrider in operation with a pistol grip.

FIG. 2B shows a side view of an example of a debrider in operation with a pistol grip. The elongate grip 112 can be moved to a deployed position (as depicted in FIG. 1) and coupled to a removable grip cover 133 as shown in FIG. 2B. A professional can hold or grasp the debrider 100 by the handle 134 including or using the truncate stub 110 and an elongate grip 112 coupled to the truncate stub 110 about a pivot point 118. Generally, such a hold can be referred to as "pistol grip". FIG. 2B shows one way a professional can use the debrider 100 in pistol grip. The elongate grip 112 can extend distally from the housing 102 such as to allow for the debrider 100 to be gripped by the elongate grip 112 and the truncate stub 110. A professional can hold the debrider 100 solely by this handle 134 or can also hold the debrider holding the handle 134 and the housing 102. In one example of a hold depicted in FIG. 2B, a professional can securely grab the handle 134 between the thumb 154 and fingers, the handle 134 being held in an arch of the hand 150. Other techniques of holding the handle 134 can be used. Pistol grip can provide a professional with enhanced power and stability in using the debrider 100. Pistol grip can also enable ergonomic rotation of the nosecone 108 relative to the housing 102 using the non-dominant hand, such as to allow for secure, anchored counterforce applied by the dominant hand 150. Using the nosecone 108 (rather than rotating the housing 102) to rotate the cutter 104 can be beneficial for certain procedures as the housing 102 is generally tethered to the one or more connection lines 142. Pistol grip can further be advantageous for certain techniques and procedures depending on the professional's facility, hand size, and other factors. It can also be used to accommodate various individual patient anatomies and pathologies.

Figure 3A:
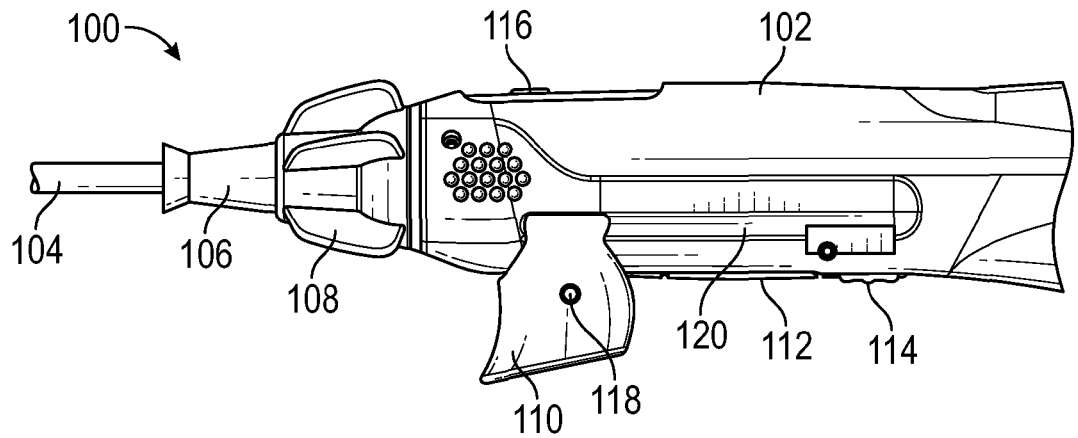
FIG. 3A is a side view of a debrider in a collapsed configuration.
Figure 3B:
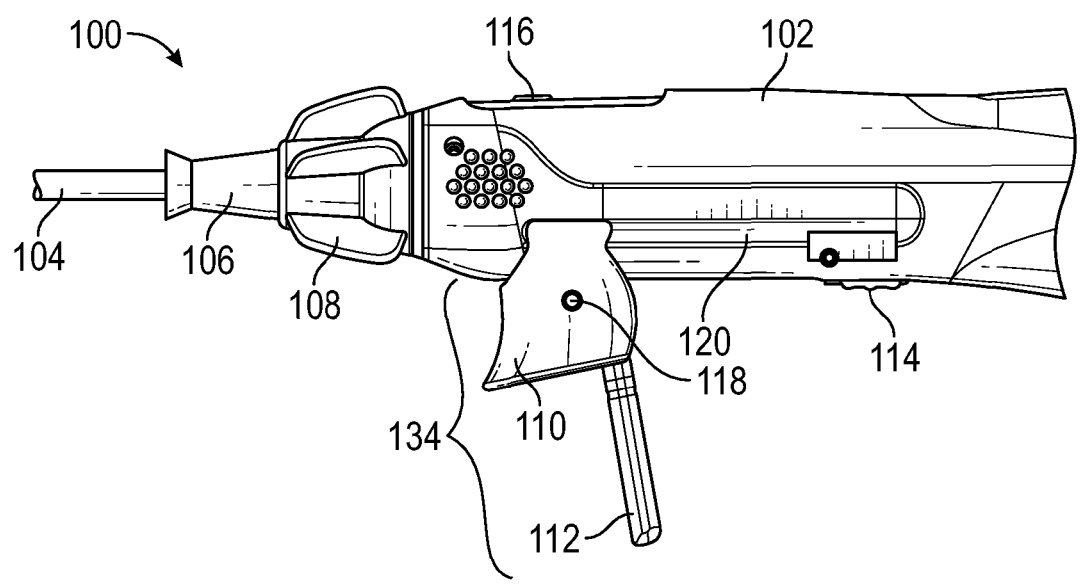
FIG. 3B is a side view of a debrider in a deployed configuration.

FIG. 3A shows a side view of an example of a debrider in a collapsed configuration. The debrider 100 can include or use the handle 134 having the truncate stub 110 and the elongate grip 112 coupled to the truncate stub 110 about the pivot point 118. The truncate stub 110 can extend distally from the housing 102 at a length within a range of about 0.1 inches to about 2 inches. In some examples, the truncate stub 110 can extend at a length within the range of about 0.5 inches to about 0.85 inches. The pivot point 118 can be a pin extending through a bore of the truncate stub 110. The pivot point 118 can also be a physical, rotatable connection between the elongate grip 112 and the truncate stub 110. The pivot point 118 can also be one or more projections on the truncate stub 110 which can mate with one or more apertures on the elongate grip 112. The pivot point 118 can also be one or more projections on the elongate grip 112 which can mate with one or more apertures on the truncate stub 110. Other suitable connections can be used to create the pivot point 118 as well. In one example, as depicted in FIG. 3A, the elongate grip 112 can pivot to be closed aft in a collapsed position and can be at least partially disposed in a cavity 103 of the housing 102. One or more grip locks 114 can be used to retain the elongate grip 112 in the collapsed position and restrict the grip 112 thereto. Additionally, as depicted in FIG. 3B, the elongate grip 112 can pivot to be opened fore in a deployed position where the grip 112 extends distally from the housing. The handle 134, having the elongate grip 112 in the deployed position, can extend distally from the housing 102 at a length within a range of about 0.2 inches to about 6 inches. In some examples, the deployed handle 134 can extend at a length within the range of about 2 inches to about 3.5 inches.

In operation and use, a professional can provide or obtain a medical device 100 for use in debridement. The professional can turn the elongate grip 112 about the pivot 118 on the truncate stub 110 to manipulate the orientation of components of the device 100. For example, the professional can turn or close the elongate grip 112 completely aft and use the device in "pen grip". In another example, the professional can turn or open the elongate grip 112 completely fore and use the device in "pistol grip". The professional can turn the elongate grip to a position between completely closed aft and completely open fore and unlock the handle 134 with respect to longitudinal sliding action along the housing 102. The professional can place the handle 134 at a preferred longitudinal position of the housing 102 and turn or open the elongate grip completely open fore to lock the handle 134 with respect to longitudinal sliding action along the housing 102. The professional can position the cutter 104 relative to a surgical site 140, and sever, cut, shave, drill, and/or remove tissue or other objects therefrom.

Figure 4A:
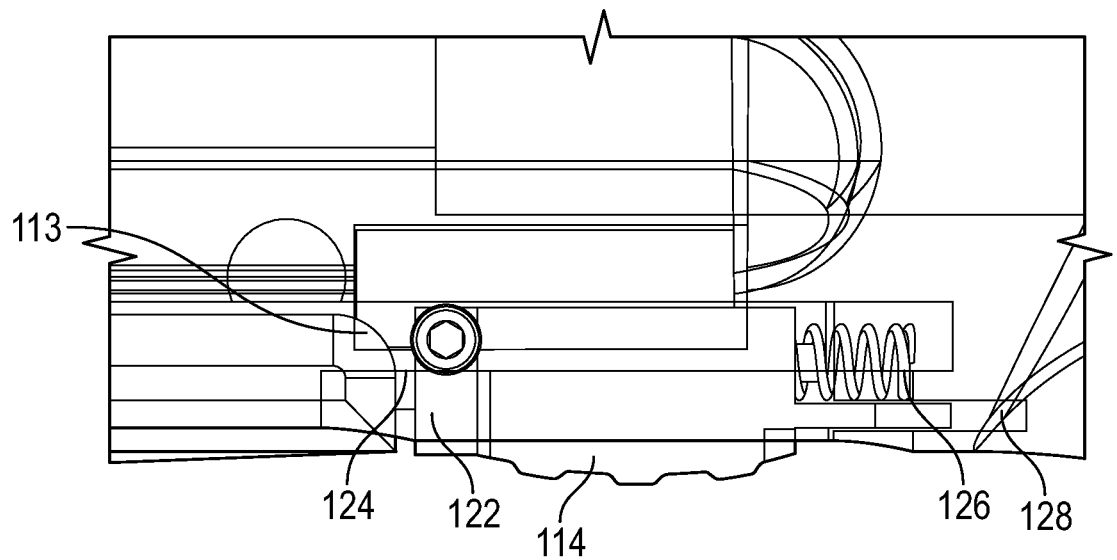
FIG. 4A is an isolated view of an elongate grip lock in a locked position.
Figure 4B:
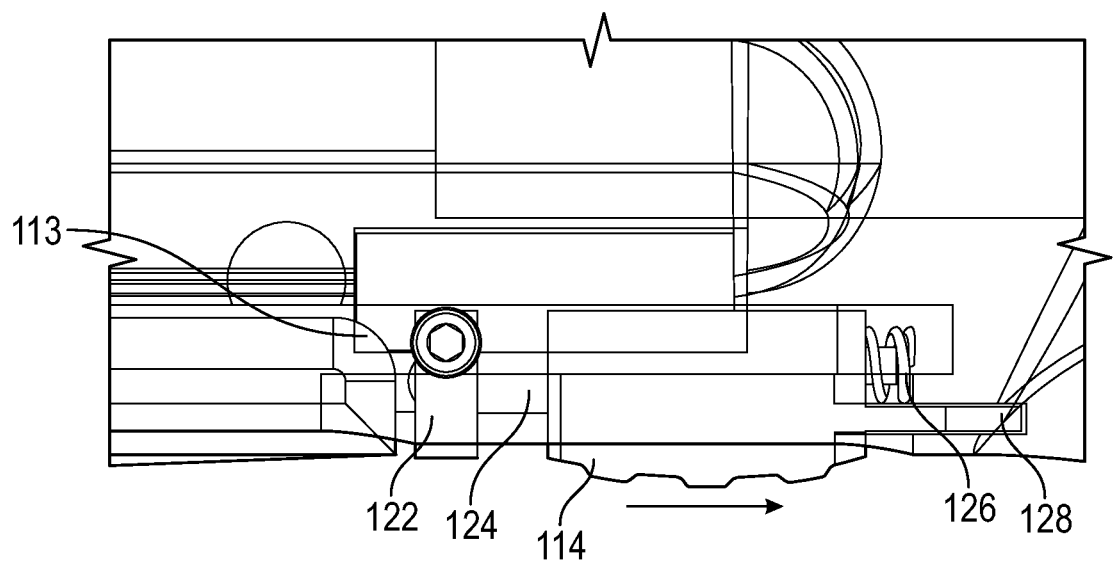
FIG. 4B is an isolated view of an elongate grip lock in an unlocked position.

FIGS. 4A & 4B show an isolated view of an example of a grip lock 114. The grip lock 114 can include or use a lock pin 124, a lock spring 126, a lock channel 128, and one or more lock guides 122. In a locked position, as depicted in FIG. 4A, the grip lock 114 can impede movement of the elongate grip 112 fore, restricting it to the collapsed position. The lock spring 126 can bias the lock 114 such as to extend the lock pin 124 at least partially into the cavity 103 of the housing 102. The elongate grip 112 can include a grip bore at an end distal to the pivot point 118. Thus, the lock pin 124 can extend at least partially through the grip bore, restricting movement of the elongate grip 112. As depicted in FIG. 4B, moving the grip lock 114 to an unbiased position can cause the lock pin 124 to retract from the bore of the elongate grip 112, restoring pivoting action to the grip 112. The grip lock 114 can include or use one or more components to secure travel of the lock 114 such as the lock channel 128 and/or the one or more lock guides 122. The elongate grip 112 and lock pin 124 can both be sized and shaped such as to allow the elongate grip 112 to be closed aft while the grip lock 114 is in the biased position, the lock 114 able to be displaced momentarily by manipulation of an elongate grip edge 113 before locking the grip 112 in the closed position. In other words, the elongate grip 112 can displace the lock pin 124 when closed aft, even where the grip 112 cannot displace the lock pin 124 when opened fore. The grip lock 114, while described herein and depicted specifically, can be one of any suitable, equivalent locking mechanisms to restrict pivoting action of the elongate grip 112. Other suitable mechanisms for locking the grip 112 can be used herewith as will be appreciated by persons skilled in the art.

Figure 5A:
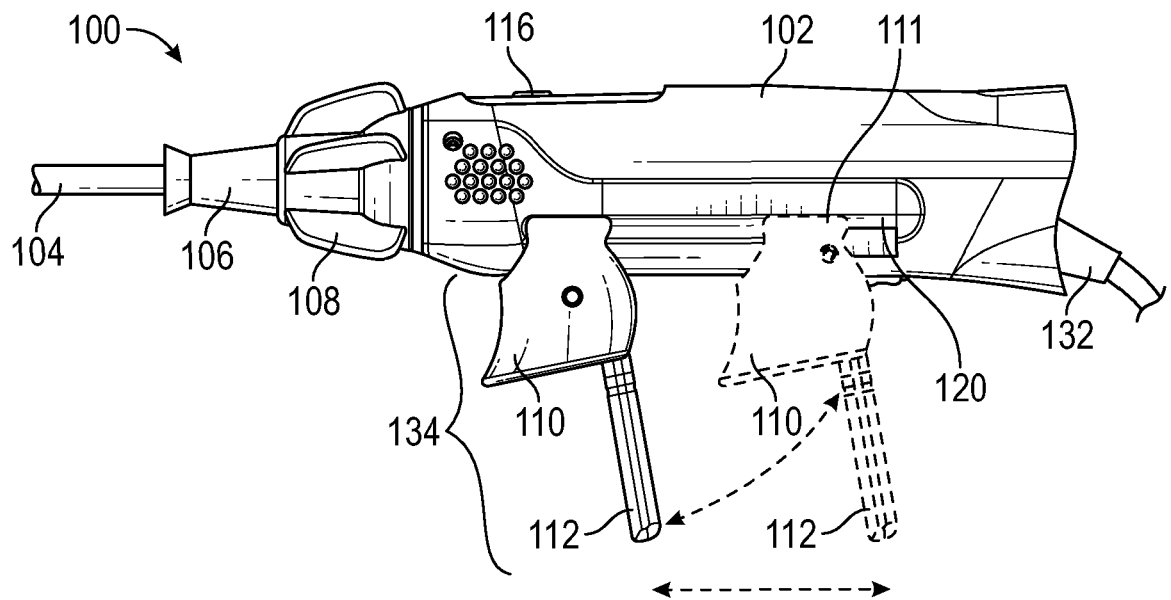
FIG. 5A is a side view of a debrider illustrating a sliding action of a handle component.

The handle 134 can be fixedly coupled to the housing 102 such as to provide a single, fixed longitudinal placement of the handle 134 and truncate stub 110. Alternatively, some examples of the debrider 100 can include or use mechanisms such as to allow for variable longitudinal placement of the handle 134 relative to the housing 102. Variable longitudinal placement of the handle 134 can be available in predefined increments, such as by incremental indentations or protrusions on the housing 102. Alternatively, variable longitudinal placement of the handle can be available continuously along the housing 102. FIG. 5A shows a side view of an example of a debrider having sliding action. In some examples, the debrider 100 can include or use one or more longitudinal grooves of the housing 120. The debrider 100 can have a pair of longitudinal grooves 120 running parallel on opposing side walls of the housing 102. The truncate stub 110 of the handle 134 can include or use one or more bars 111 sized and shaped to ride the one or more longitudinal grooves 120. Where the bars 111 of the truncate stub 110 ride the grooves 120, the handle 134 can be slidingly paired to the housing 102. As such, the handle 134 can slide longitudinally along a length of the grooves 120. While the connection is described herein as having bars 111 riding grooves 120, other equivalent connections enabling longitudinal sliding motion of the handle 134 relative to the housing 102 are commonly known by persons skilled in the art and can be used herewith. For instance, alternatively or additionally the grooves 120 can be on the handle 134 and the bars 111 can be on the housing 102.

Figure 5B:
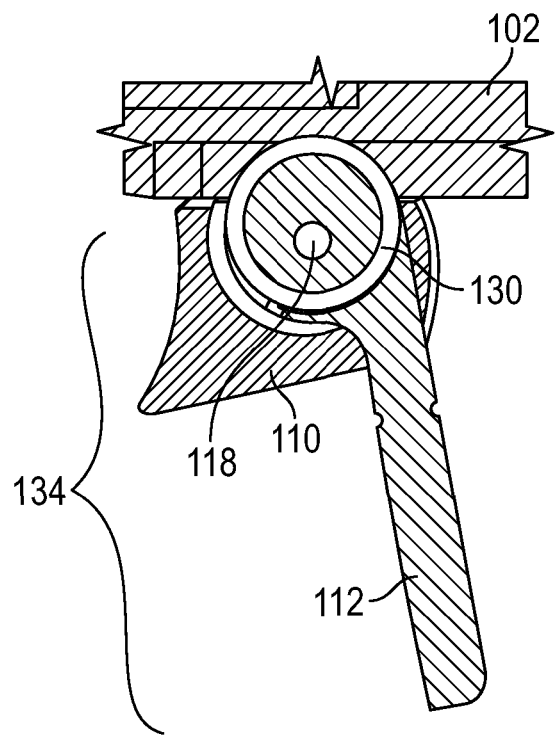
FIG. 5B is an isolated cross-section view of an elongate grip.

FIG. 5B shows an isolated cross-section view of an example of an elongate grip. The handle 134 can include or use the elongate grip 112 being at least partially housed within the truncate stub 110. The elongate grip 112 can further include or use an eccentric locking cam 130. The cam 130 can be located eccentrically relative to the pivot point 118 and can function to engage on the housing 102 when the elongate grip 112 is in the deployed position. Such an engagement of the cam 130 on the housing 102 can restrict longitudinal movement of the handle 134 relative to the housing 102. The cam 130 can include or use a rubber bearing or surface finish such as to secure the engagement of the cam 130 with the housing 102. The cam 130 can include or use a compressible material, a tacky material, a roughened surface finish, or other materials or finishes such as to secure the engagement of the cam 130 with the housing 102. Turning the elongate grip 112 completely fore to the deployed position can cause the handle 134 to lock with respect to the sliding action, such as sliding action of the bars 111 within the grooves 120. The locking of sliding action as such can occur at several longitudinal points along the housing 102. Such locking can occur continuously along the housing 102. Alternatively, such locking can occur digitally at one of several predetermined positions along the housing 102. Thus, longitudinal sliding of the handle 134 or truncate stub 110 can be restricted where the handle is completely deployed. Where the debrider 100 includes or uses mechanisms to allow for variable longitudinal placement of the handle 134 relative to the housing 102, placing the elongate grip 112 in the collapsed position can restrict travel of the truncate stub 110 relative to the housing 102. Thus, longitudinal sliding of the handle 134 or truncate stub 110 can also be restricted where the handle is completely collapsed.

Figure 6A:
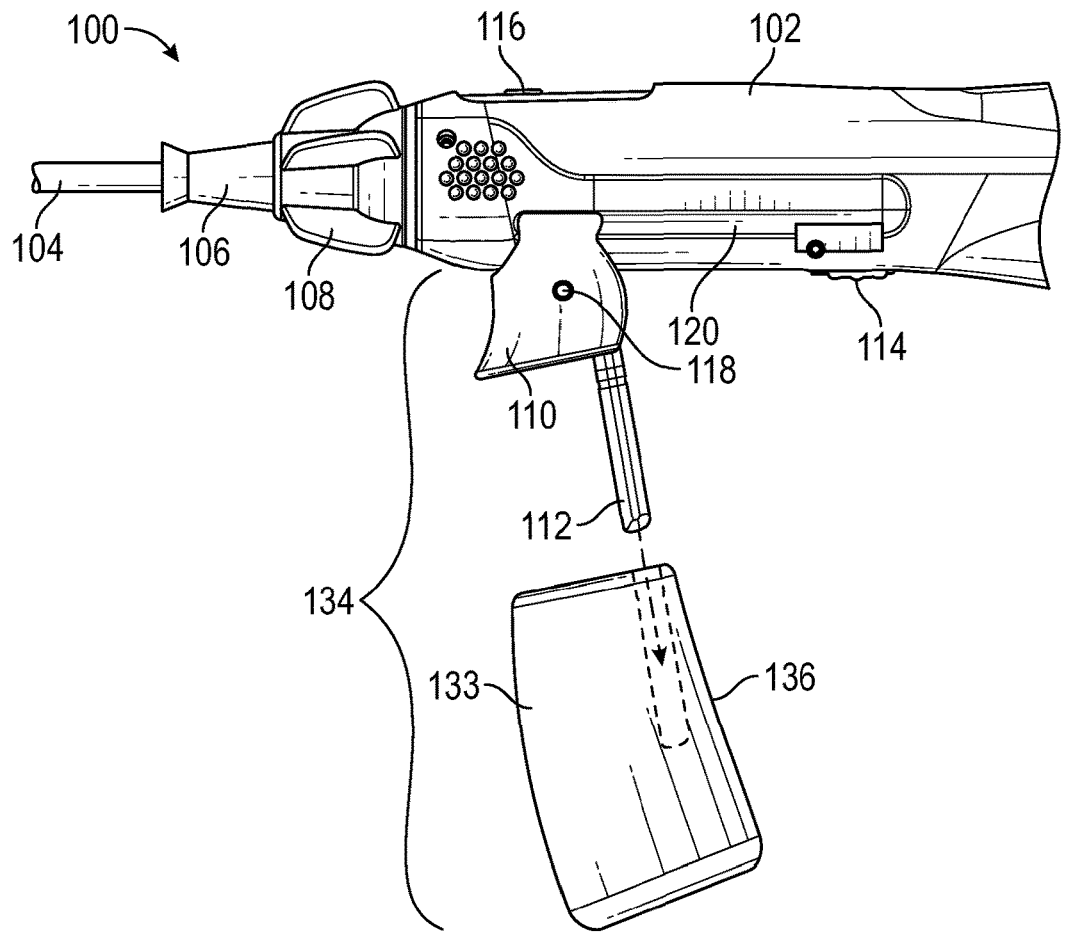
FIG. 6A is a side view of a debrider unpaired with a grip cover.
Figure 6B:
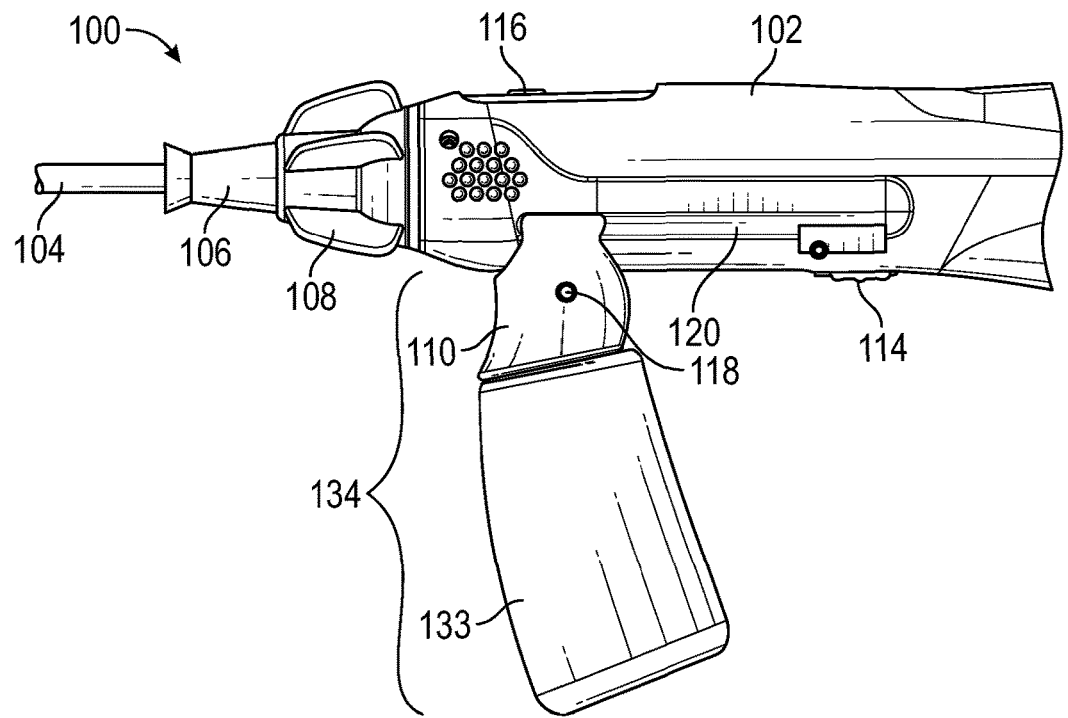
FIG. 6B is a side view of a debrider paired with a grip cover.

FIG. 6A shows a side view of an example of a debrider unpaired with a grip cover. The debrider 100 with the elongate grip 112 in the deployed position can be paired to a grip cover 133. The grip cover 133 can include a grip cover bore 136 that is sized and shaped such as to be substantially conformal to an outer shape of the elongate grip 112. The grip 112 and grip cover bore 136 can be sized and shaped such as to provide sufficient pressure between the grip 112 and grip cover 133 for prevention of accidental twisting or unpairing during the procedure. The grip cover 133 can be formed of one of several thermoplastic elastomers. Other materials can also be used to form the grip cover 133. The grip cover 133 can be slid over the elongate grip 112, as exemplified in FIG. 6B.

Figure 7C:
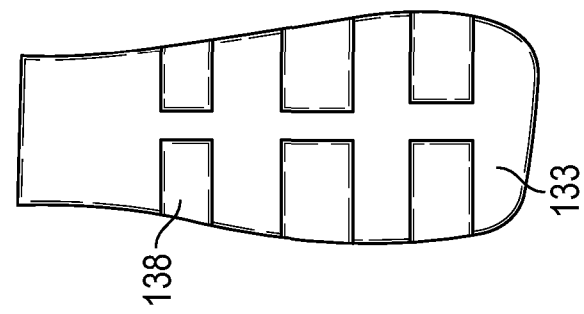
FIG. 7C is a front view of a grip cover.
Figure 7B:
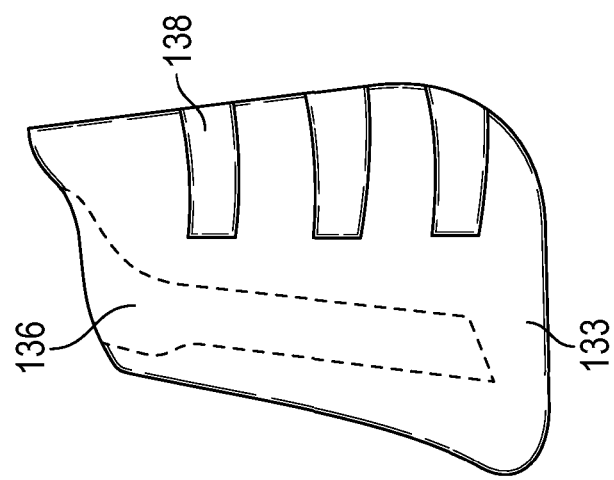
FIG. 7B is a side view of a grip cover.
Figure 7A:
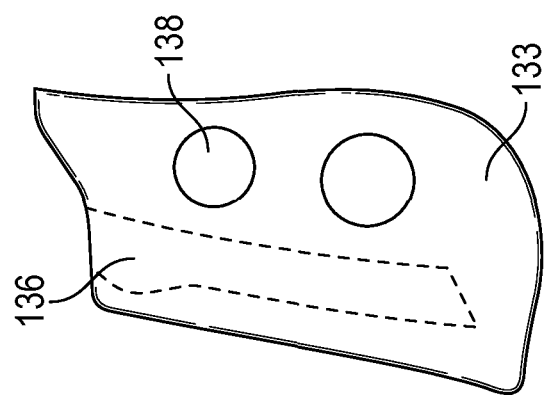
FIG. 7A is a side view of a grip cover.
Figure 8A:
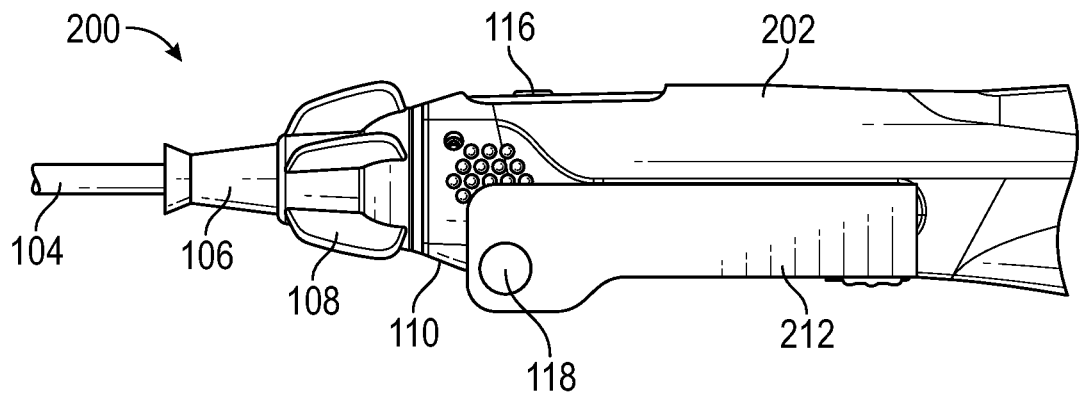
FIG. 8A is a side view of a debrider in a collapsed configuration.
Figure 8B:
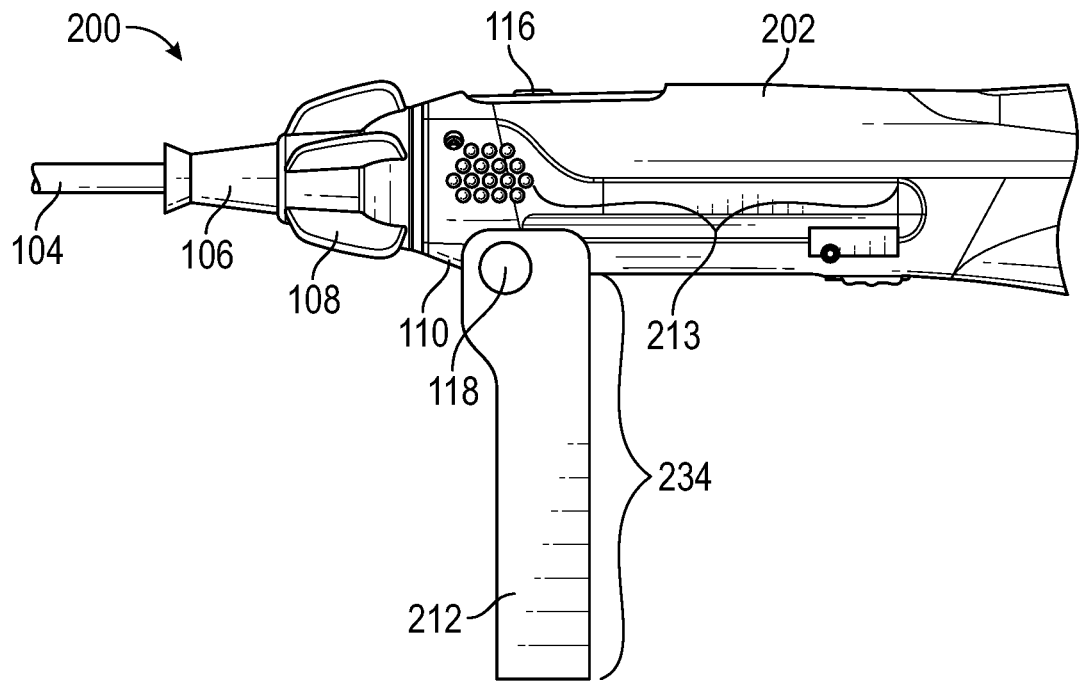
FIG. 8B is a side view of a debrider in a deployed configuration.
Figure 8E:
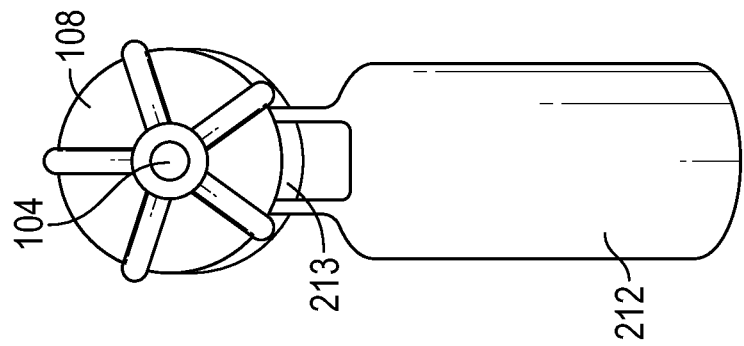
FIG. 8E is a front view of a debrider in a deployed configuration.
Figure 8D:
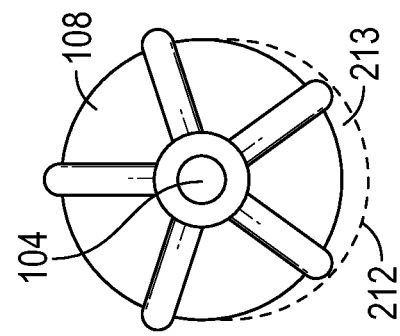
FIG. 8D is a front view of a debrider in a collapsed configuration.
Figure 8C:
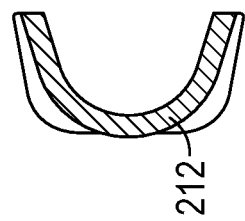
FIG. 8C is a top view of an elongate grip.

FIGS. 7A-7C show further examples of the grip cover. The grip cover 133 can be constructed using one of several manufacturing techniques to include one or more cavities 138. The cavities 138 can allow the grip cover 133 to be reduced in weight and can prevent sinks and other manufacturing defects. Grip covers 133 with various outer sizes and shapes can be available to accommodate the professional's hand size, finger length, facility, and other factors. The grip cover 133 can be reusable, such as can be washable or autoclavable. Alternatively, the grip cover 133 can be disposable.

FIGS. 8A-E depict another an example of a debrider. Debrider 200 is similar to debrider 100, but contains a housing recess 213 which can be enclosed by the elongate grip 212 of the handle 234. An elongate grip 212 can be c-shaped, u-shaped, v-shaped, or can be otherwise shaped such as to mate with the housing recess 213. Alternatively, the elongate grip 212 can be sized and shaped such as to enclose the housing 202 where the housing 202 does not have a housing recess 213. The elongate grip 212 in the deployed position can extend distally from the housing 202 at a length within a range of about 0.2 inches to about 6 inches. In some examples, the deployed elongate grip 212 can extend at a length within the range of about 2 inches to about 3.5 inches. Elongate grip 212 can be sized and shaped such as to allow for secure, ergonomic grip without the need to utilize grip cover 133. The housing 202 or housing recess 213 can contain indentations or protrusions sized and shaped to mate with indentations or protrusions of the elongate grip 212 to secure or lock the grip 212 in the closed position (shown in FIG. 8A).

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37

C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical device for tissue removal, the medical device comprising:
    a housing;
    a shaft extending at least partially through the housing and extending distally out of the housing, the shaft including a cutter configured to be driven by an actuator or driver to cut tissue;
    a handle comprising:
        a truncate stub connected to and translatable along the housing; and
        an elongate grip pivotably coupled to the truncate stub and translatable with the truncate stub along the housing.

2. The medical device of claim 1, wherein the elongate grip is configured to pivotable to move between:
    a collapsed position wherein the elongate grip is at least partially located in a cavity in the housing; and
    a deployed position wherein the elongate grip extends distally and laterally outward from the elongate housing and extends from the truncate stub.

3. The medical device of claim 2, wherein the elongate includes at least one longitudinal groove, the truncate stub located at least partially within the longitudinal groove such that the truncate stub is translatable relative to the housing along the longitudinal groove.

4. The medical device of claim 1, wherein the shaft includes a lumen connectable to a vacuum port to receive remote suction in the lumen.

5. The medical device of claim 1, comprising:
    a grip cover configured to slide over the elongate grip adjacent the truncate stub to, together with the truncate stub, form an extended grip.

* * * * *